United States Patent [19]

Uchida

[11] Patent Number: 5,135,720
[45] Date of Patent: Aug. 4, 1992

[54] REACTION CHAMBER FOR AMINO-TERMINAL SEQUENCE ANALYSIS OF PROTEINS OR PEPTIDES

[75] Inventor: Toyoaki Uchida, Tokyo, Japan
[73] Assignee: Seiko Instruments Inc., Japan
[21] Appl. No.: 530,203
[22] Filed: May 30, 1990
[51] Int. Cl.$^5$ .................. B03C 1/02; C12N 13/00; C12M 1/34; G01N 33/553
[52] U.S. Cl. .................. 422/107; 422/116; 422/69; 436/526; 435/291; 435/173; 435/180; 435/287; 210/222
[58] Field of Search .............. 422/107, 186.01, 106, 422/108, 70, 116, 69; 210/222; 436/526; 435/287, 291, 173, 180

[30] Foreign Application Priority Data

May 23, 1989 [JP] Japan .................. 1-129740

[56] References Cited

U.S. PATENT DOCUMENTS

| | | | |
|---|---|---|---|
| 4,141,687 | 2/1979 | Forrest et al. | 210/222 |
| 4,181,853 | 1/1980 | Abu-Shumays et al. | 422/69 |
| 4,375,407 | 3/1983 | Kronick | 436/526 |
| 4,649,116 | 3/1987 | Daly et al. | 435/287 |
| 4,695,393 | 9/1987 | Whitehead et al. | 436/526 |
| 4,710,472 | 12/1987 | Saur et al. | 435/287 |
| 4,855,045 | 8/1989 | Reed | 210/222 |
| 4,865,730 | 9/1989 | Lám et al. | 210/222 |

Primary Examiner—Robert J. Warden
Assistant Examiner—T. A. Trembley
Attorney, Agent, or Firm—Bruce L. Adams; Van C. Wilks

[57] ABSTRACT

A reaction chamber utilizes a sample carrier composed of a magnetic core and a surface coating effective to support sample of protein or peptide. The sample carrier is floated magnetically by means of electromagnets positioned within a reaction vessel. Edman reagnet is applied to the sample to effect amino acid sequence analysis of protein or peptide from amino-terminal. By such construction, reaction efficiency of repeated production of thiazolinon amino-acid derivatives is increased so as to increase number of identified amino acids, thereby enabling microanalysis of sample.

12 Claims, 3 Drawing Sheets

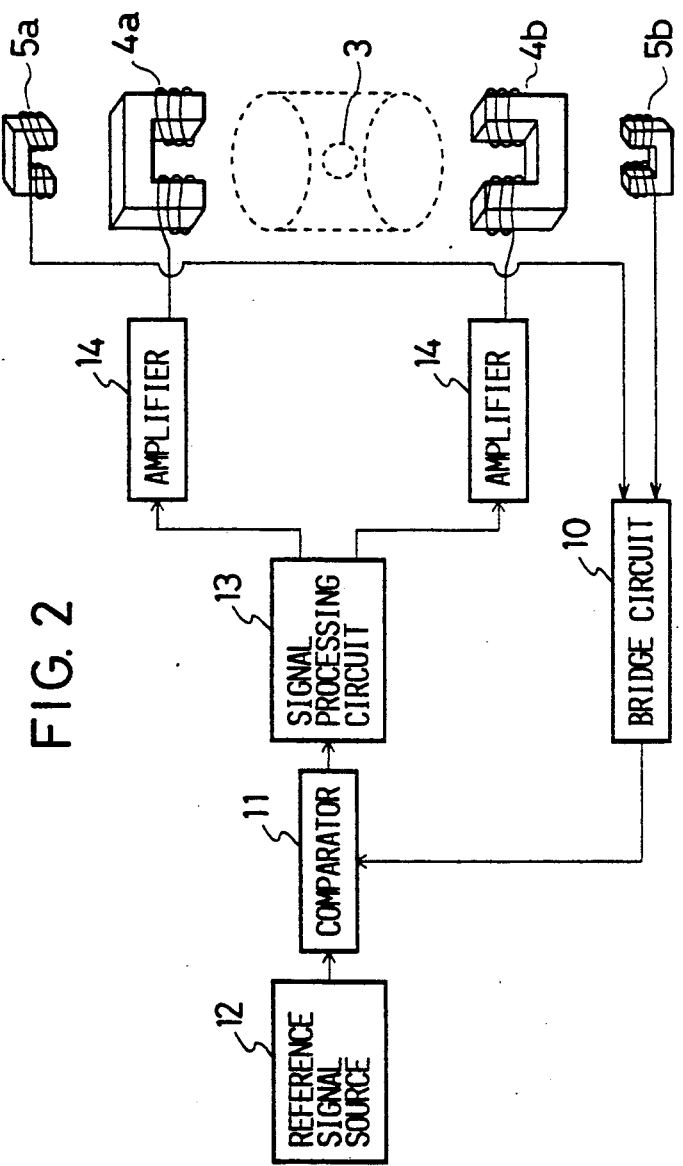
FIG. 2
FIG. 1
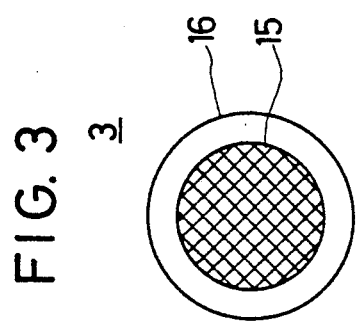
FIG. 3

REACTION CHAMBER FOR AMINO-TERMINAL SEQUENCE ANALYSIS OF PROTEINS OR PEPTIDES

BACKGROUND OF THE INVENTION

The present invention relates to a reaction chamber carrying out reactions which sequentially produce 2-anilino-5-thiazolinon amino acid derivatives in an analyzer which automates amino-terminal sequence analysis of protein or peptide.

FIGS. 5 and 6 show two kinds of the conventional reaction chamber carrying out reactions which sequentially produce thiazolinon amino acid derivatives based on the Edman reaction.

The conventional reaction chamber of FIG. 5 is constructed such that sample is adsorped in a glass filter 20 on a membrane filter 19 sandwiched by a pair of glass blocks 18a and 18b within a frame 17, and reagent or solvent is applied to the sample through a flow path in the center of the glass blocks according to procedure of the Edman reaction.

The other conventional reaction chamber shown in FIG. 6 comprises a reaction chamber 24 connected to a vacuum pump 22 and to a nitrogen gas bottle 23 through a three-way switch valve 21 to vacuum the reaction chamber or to fill the reaction chamber with nitroqen gas. The reaction chamber 24 contains a glass cup 26 rotatable by a motor 25, a supply line 27 for delivering reagent and solvent needed for reaction, into the glass cup 26 and a discharge line 28 for removing this reagent and solvent.

However, with regard to the FIG. 5 conventional reaction chamber, the sample is supported between glass fibers of the glass filter 20 and therefore the reagent or solvent cannot be efficiently distributed to the sample. Hence the efficiency of reactions become lower. Thereby, repetitive yield in the sequence analysis is reduced. Such tendency becomes remarkable in the case of treating a micro amount of sample to thereby make unable the analysis. Further, various kinds of reagents and solvents are supplied through a common flow path to the protein sample for the reaction. Therefore, these reagents may be contaminated with each other.

With regard to the FIG. 6 conventional reaction chamber, the structure for rotation must be equipped in the vacuum chamber. Thereby, the maintenance of the analyzer is complicated. Especially, when the glass cup has a small dimension for treating a micro amount of the sample, it is difficult to maintain the stable rotation of such small glass cup.

SUMMARY OF THE INVENTION

An object of the present invention is to, therefore, eliminate the above noted drawbacks of the prior art.

According to the present invention, the reaction chamber is comprised of a reaction vessel made of nonmagnetic material having a reaction space and inlet and outlet of fluid such as solvent, a sample carrier disposed in the reaction space and comprised of a magnetic material and a sample supporting material covering the magnetic material, magnetic means disposed inside the reaction chamber for floating and holding the sample carrier by magnetic force to shift the sample carrier in a vertical axis direction, and a sensor for detecting a position of the sample carrier.

In such reaction chamber having the above construction, the sample of protein or peptide is uniformly distributed on the surface of the sample carrier in the reaction space, and the sample carrier is floated and held to shift in the vertical axis direction so as to increase the reaction efficiency between the sample and the reagent or solvent.

BRIEF DESCRIPTION OF THE DRAWINGS

FIGS. 1-4 show embodiments of the reaction chamber according to the present invention, wherein
FIG. 1 is a sectional view of the reaction chamber,
FIG. 2 is a control block diagram of electromagnets 4 and position sensors 5,
FIG. 3 is a sectional view of a sample carrier;
FIG. 4 shows a separation pattern of a standard mixture of phenylthiocarbamyl amino acid derivatives.

DETAILED DESCRIPTION OF EMBODIMENTS

Figure 4:
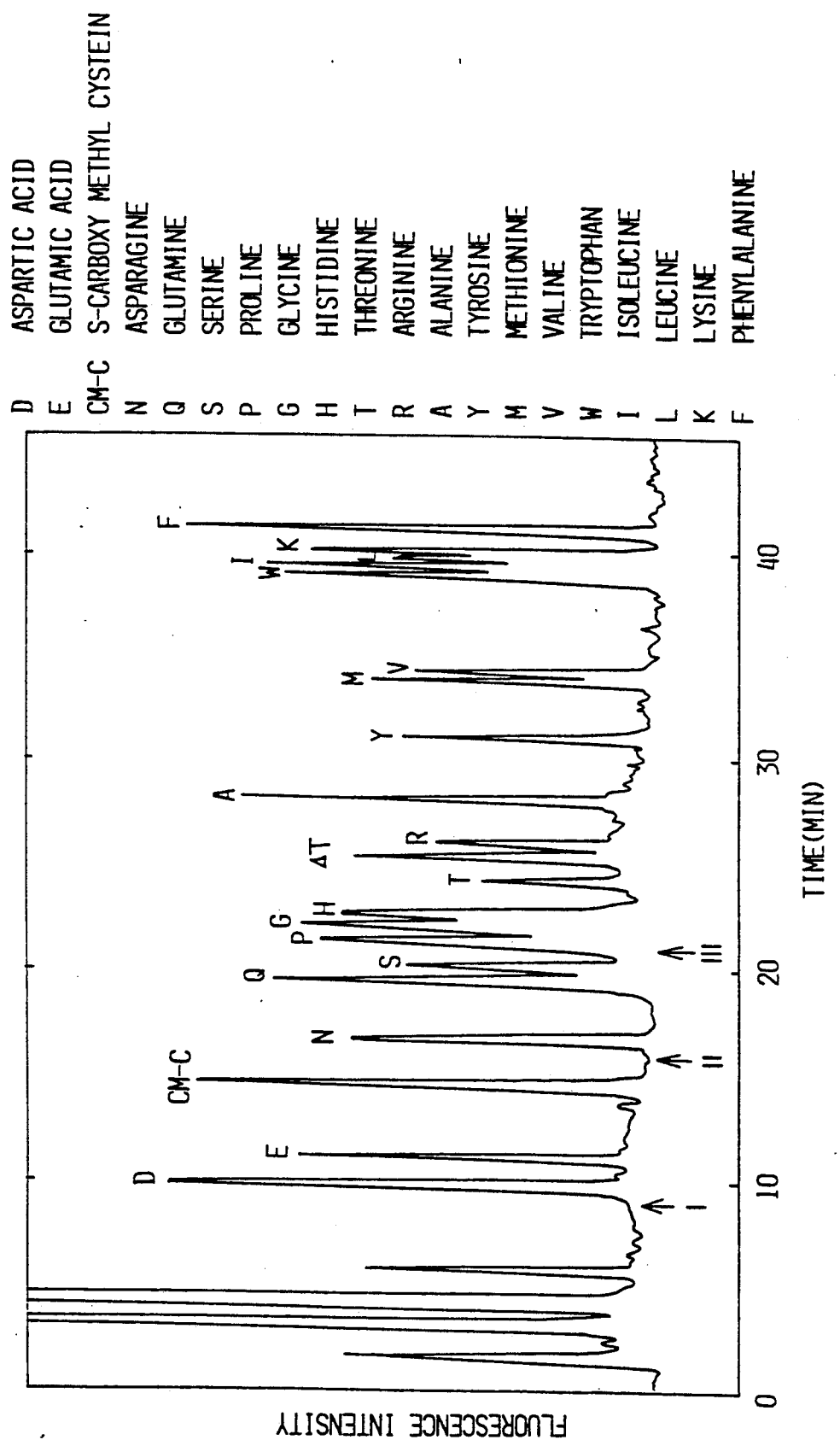
Figure 5:
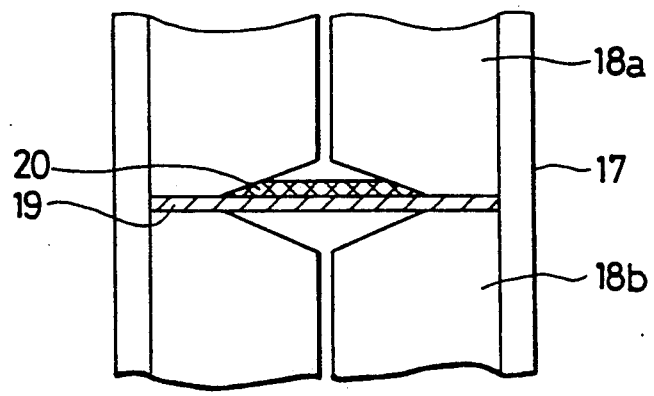
FIGS. 5 and 6 are sectional views of the conventional reaction chamber.
Figure 6:
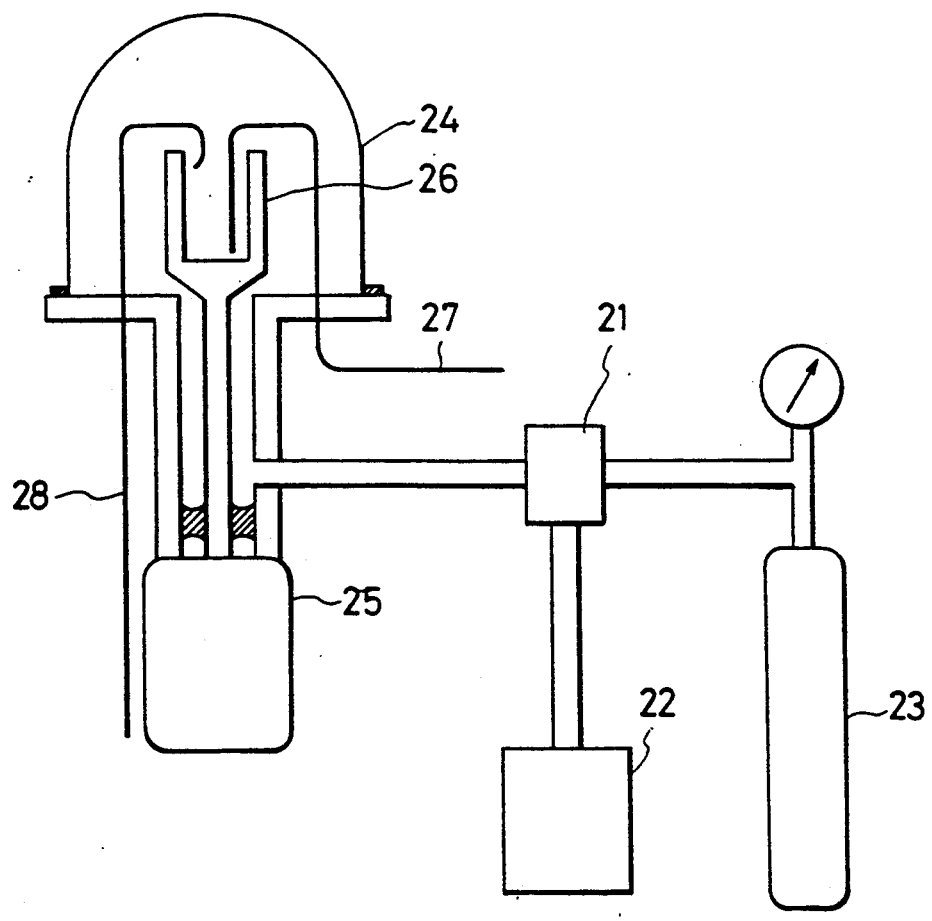

Hereinafter, embodiments of the present invention will be described in conjunction with the drawings.

Firstly, one embodiment is described to show how to float and hold a sample carrier in a reaction chamber. In the reaction chamber 1 shown in FIG. 1, a reaction vessel 2 is provided therein with a sample carrier 3 which carries a protein sample and is composed of magnetic material and is floated inside the vessel 2. This floating and holding is effected by magnetic force generated by electromagnets 4 (magnetic means) and the position of the sample carrier is monitored by position sensors 5.

The electromagnets 4 are disposed within the walls of the reaction vessel 2 which is divided into upper and lower parts which are coupled to define the reaction space 6 to contain therein the sample carrier 3.

Further, the reaction vessel 2 is provided with an upper fluid path 7 and a lower fluid path 8 so as to charge and discharge reagent and solvent needed for the reactions. The reaction vessel 2 is supported by a retainer 9.

Next, the description is given with reference to FIG. 2 for how to control the floating and holding of the sample carrier 3 in the vertical axis by means of the electromagnets 4 and position sensors 5. Firstly, a position sensor 5a detects a distance $G_1$ between an electromagnet 4a and the sample carrier 3 floated by magnetic force generated by the electromagnet 4a and another electromagnet 4b, and another sensor 5b detects a distance $G_2$ between the electromagnet 4b and the sample carrier 3. In order to hold the sample carrier 3 at a mid point between the electromagnets 4a and 4b, a bridge circuit 10 processes a pair of detection signals representative of the detected distances $G_1$ and $G_2$, and then a comparator 11 compares the processed signal with a reference signal from a reference signal source 12, and further a signal processing circuit 13 calculates appropriate values of electric currents for the electromagnets 4a and 4b based on the compared results. Each amplifier 14 amplifies electric currents to the electromagnets according to the calculated values so as to control the magnitude of the magnetic forces generated from the electromagnets 4a and 4b to thereby equalize the distances $G_1$ and $G_2$ with each other. Further, when the sample carrier 3 is to be displaced upward or downward in the vertical direction, the signal processing circuit 13 operates to calculate appropriate current values effective to enable the electromagnetes 4a and 4b to adjust the distances $G_1$ and $G_2$ through the amplifiers 14.

In the inventive reaction chamber, applied reagents and solvents can be efficiently acted to the sample on the sample carrier.

Next, the description is given for how to sequentially produce thiazolinon amino acid derivatives from protein sample carried on the sample carrier and how to detect the derivatives.

As shown in FIG. 3, the sample carrier 3 is comprised of a spherical ferrite core 15 and a glass coating 16 formed thereon as the sample supporting material. In such structure, the ferrite core 15 may be of spherical, cubic, cylindrical, spheroidic or other shape.

The sample supporting material coated on the surface of the ferrite core 15 may be composed of glass, ceramics and polymer material such as polyvinylidenedifluoride and polymethyltrifluoropropylsiloxane.

The following procedure is based on an ordinary automated gas-phase Edman method. The sample carrier 3 of 5 mm diameter is treated with polybrene (hexadimethrin bromide) and then is applied with 5 $\mu$l of 70% formic acid containing 1 pico (pico:$10^{-12}$) mole of myoglobin, and thereafter protein sample is dried. Subsequently, application of coupling reagent, buffer vapor, washing solvent, cleavage reagent and extraction solvent is delivered to the reaction chamber according to analysis program (Table 1) of the commercially available automated gas-phase sequence analyzer. Sequentially obtained thiazolinon amino acid derivatives are detected according to fluorescence analysis using 4-amino fluorescein. Namely; 75 $\mu$l of methanol containing 1% of pyridine and 25 $\mu$l of methanol containing 30 pico mole of 4-amino fluorescein are successively added to 150 $\mu$l of butyl chloride containing thiazolinon amino acid derivatives, and the mixture is dried. Next, 25 $\mu$l of methanol containing 30 pico mole of 4-amino fluorescein is added again, and the mixture is dried after 10 minutes of standing. This dried sample is dissolved by 50 $\mu$l of methanol. A 25 $\mu$l portion of the solution is applied to analysis using liquid chromatograph and fluorophotometric detector. Analysis condition is shown in table 2. Further, FIG. 4 shows separation pattern of the standard mixture of 20 kinds of phenylthiocarbamyl amino acid derivatives obtained by the above described procedure. An amount of the respective derivatives is in the order of 10 to 15 femto (femto:$10^{-15}$) mole. All of the derivatives can be separated and identified.

TABLE 1

Cycle length: 32 steps
Runtime: 43 mins 32 secs

| Step | Function | Value | Elapsed Time |
|---|---|---|---|
| 1 | Prep R2 | 6 | 0 min 6 sec |
| 2 | Deliver R2 | 20 | 0 min 26 sec |
| 3 | Prep R1 | 6 | 0 min 32 sec |
| 4 | Deliver R1 | 2 | 0 min 34 sec |
| 5 | Argon Dry | 40 | 1 min 14 sec |
| 6 | Deliver R2 | 400 | 7 min 54 sec |
| 7 | Prep R1 | 6 | 8 min 0 sec |
| 8 | Deliver R1 | 2 | 8 min 2 sec |
| 9 | Argon Dry | 40 | 8 min 42 sec |
| 10 | Deliver R2 | 400 | 15 min 22 sec |
| 11 | Prep R1 | 6 | 15 min 28 sec |
| 12 | Deliver R1 | 2 | 15 min 30 sec |
| 13 | Argon Dry | 40 | 16 min 10 sec |
| 14 | Deliver R2 | 400 | 22 min 50 sec |
| 15 | Argon Dry | 120 | 24 min 50 sec |
| 16 | Deliver S1 | 60 | 25 min 50 sec |
| 17 | Deliver S2 | 200 | 29 min 10 sec |

TABLE 1-continued

Cycle length: 32 steps
Runtime: 43 mins 32 secs

| Step | Function | Value | Elapsed Time |
|---|---|---|---|
| 18 | Argon Dry | 120 | 31 min 10 sec |
| 19 | Load R3 | 4 | 31 min 14 sec |
| 20 | Argon Dry | 4 | 31 min 18 sec |
| 21 | Pause | 300 | 36 min 18 sec |
| 22 | Load S2 | 6 | 36 min 24 sec |
| 23 | Block Flush | 6 | 36 min 30 sec |
| 24 | Argon Dry | 120 | 38 min 30 sec |
| 25 | Prep Transfer | 30 | 29 min 0 sec |
| 26 | Deliver S1 | 9 | 39 min 9 sec |
| 27 | Transfer w/S3 | 52 | 40 min 1 sec |
| 28 | Pause | 20 | 40 min 21 sec |
| 29 | Transfer w/Argon | 40 | 41 min 1 sec |
| 30 | End Transfer | 1 | 41 min 2 sec |
| 31 | Deliver S3 | 30 | 41 min 32 sec |
| 32 | Argon Dry | 120 | 43 min 32 sec |

(Extracted from 477 A type manual of Applied Biosystems Inc., Ltd.)
R1: 5% phenylisothiocyanate/heptane
R2: 12.5% trimethylamine/water
R3: trifluoroacetic acid
S1: n-heptane
S2: ethyl acetate
S3: butyl chloride

TABLE 2

ANALYSIS CONDITIONS FOR LIQUID CHROMATOGAPH

Column: Capcell Pack (AG) C18 produced by Shiseido co., Ltd. $\phi$ 4.6 mm $\times$ 150 mm
column temperature: 43° C.
Detector: spectrofluorophotometer RT-540 produced by Shimazu Seisakusho Co., Ltd.
Excitation wavelength: 494 mm
Emission wavelength: 513 mm
Pump: Waters 600E system
Flow rate: total 0.8 m/min
Gradient program: (A) 10 mM sodium phosphate buffer
(B) methanol
(C) acetonitrile

| time (min) | (A) % | (B) % | (C) % |
|---|---|---|---|
| 0.0 | 79 | 20 | 1 |
| 0.1 | 75 | 23 | 2 |
| 14.0 | 75 | 23 | 2 |
| 19.0 | 71 | 19 | 12 |
| 34.0 | 71 | 12 | 19 |
| 40.0 | 50 | 25 | 25 |
| 45.0 | 79 | 20 | 1 |
| 65.0 | 79 | 20 | 1 |

As described above, in the reaction chamber according to the present invention, the sample carrier is floated and positioned in the reaction vessel, thereby reagents and solvents are efficiently and uniformly applied to the sample, as well as cross contamination of the used reagents and solvents can be avoided as much as possible.

What is claimed is:

1. A reaction chamber comprising:
   a reaction vessel composed of nonmagnetic material for defining a reaction space and having an inlet and outlet for charging and discharging fluid;
   a sample carrier disposed in the reaction space;
   magnetic means disposed inside the reaction vessel for generating magnetic forces effective to float the sample carrier into a desired position wherein the sample carrier is not in contact with the reaction vessel; and
   a sensor for detecting the position of the sample carrier.

2. A reaction chamber according to claim 1; wherein the sample carrier is composed of a magnetic material and a sample supporting material formed on a surface of the sample carrier.

3. A reaction chamber according to claim 2; wherein the sample supporting material is composed of material selecting from glass, ceramics and polymers including poly vinylidene difluoride and polymethyltrifluoropropylsiloxane.

4. A reaction chamber according to claim 2; wherein the sample carrier has a spheric or spheroidic shape.

5. A reaction chamber according to claim 1; wherein the reaction vessel has a plurality of divided parts.

6. A reaction chamber according to claim 1; including means responsive to the detection of the position of the sample carrier by the sensor for controlling the magnetic means to maintain the desired position of the sample carrier.

7. A reaction chamber comprising:
 a reaction vessel composed of nonmagnetic material and defining a reaction space having a fluid inlet and a fluid outlet;
 a sample carrier disposable in the reaction space;
 generating means for generating magnetic forces in the reaction space effective to float the sample carrier in the reaction space; and
 means for sensing the position of the sample carrier in the reaction space and for controlling the generating means to maintain the sample carrier solely by magnetic forces in a desired position completely out of contact with the reaction vessel.

8. The reaction chamber according to claim 7; wherein the means for sensing comprises sensor for producing signals corresponding to the position of the sample carrier, and circuit means for processing the signals to produce contol signals for controlling the generating means.

9. The reaction chamber according to claim 7, wherein the sample carrier comprises magnetic material and has sample supporting material on a surface thereof.

10. A reaction chamber according to claim 9, wherein the sample supporting material is composed of material selecting from glass, ceramics and polymers including poly vinylidene difluoride and polymethyltrifluoropropylsiolxane.

11. The reaction chamber according to claim 7, wherein the sample carrier is spherical in shape.

12. The reaction chamber according to claim 7, wherein the reaction vessel comprises a plurality of connected parts.

* * * * *